United States Patent
Maurel

(10) Patent No.: US 8,877,237 B2
(45) Date of Patent: Nov. 4, 2014

(54) REVERSE MICELLE SYSTEM COMPRISING NUCLEIC ACIDS AND USE THEREOF

(75) Inventor: Jean-Claude Maurel, Castries (FR)

(73) Assignee: Medesis Pharma, Baillargues (FR)

( * ) Notice: Subject to any disclaimer, the term of this patent is extended or adjusted under 35 U.S.C. 154(b) by 0 days.

(21) Appl. No.: 13/636,452

(22) PCT Filed: Mar. 24, 2011

(86) PCT No.: PCT/EP2011/054512
§ 371 (c)(1),
(2), (4) Date: Nov. 12, 2012

(87) PCT Pub. No.: WO2011/117334
PCT Pub. Date: Sep. 29, 2011

(65) Prior Publication Data
US 2013/0065944 A1    Mar. 14, 2013

Related U.S. Application Data

(60) Provisional application No. 61/317,050, filed on Mar. 24, 2010.

(30) Foreign Application Priority Data

Mar. 24, 2010  (EP) .................................. 10305299

(51) Int. Cl.
*A61K 9/127* (2006.01)
*C12N 15/11* (2006.01)
*A61K 48/00* (2006.01)

(52) U.S. Cl.
CPC .............. *A61K 9/1272* (2013.01); *A61K 9/1277* (2013.01); *Y10S 514/938* (2013.01)
USPC ......... 424/450; 514/938; 514/44 A; 514/44 R

(58) Field of Classification Search
USPC ....................... 424/450; 514/44 A, 44 R, 938
See application file for complete search history.

(56) References Cited

FOREIGN PATENT DOCUMENTS

| | | |
|---|---|---|
| EP | 1652513 | 5/2006 |
| WO | WO 03/030865 | 4/2003 |
| WO | WO 03/047493 | 6/2003 |
| WO | WO 2008/124634 | 10/2008 |
| WO | WO 2009/051837 | 4/2009 |

OTHER PUBLICATIONS

Crombez, L. et al. "Targeting cyclin B1 through peptide-based delivery of siRNA prevents tumour growth" *Nucleic Acids Research*, 2009, pp. 4559-4569, vol. 37, No. 14.
Musacchio, T. et al. "Effective Stabilization and Delivery of siRNA: Reversible siRNA-Phospholipid Conjugate in Nanosized Mixed Polymeric Micelles" *Bioconjugate Chemistry*, 2010, pp. 1530-1536, vol. 21.
Roh, Y. H. et al. "DNAsomes: Multifunctional DNA-based Nanocarriers" *Small*, Jan. 3, 2011, pp. 74-78, vol. 7, No. 1.
Written Opinion in International Application No. PCT/EP2011/054512, Apr. 16, 2012, pp. 1-7.

*Primary Examiner* — Jon E Angell
(74) *Attorney, Agent, or Firm* — Saliwanchik, Lloyd & Eisenschenk

(57) ABSTRACT

The present invention relates to reverse micelle system based on sterols, acylglycerols, phospholipids or sphingolipids and nucleic acids. The reverse micelle system of the invention is able to cross mucosa and cellular membranes. It thus allows vectorization of nucleic acids to target sites. It is advantageously useful in the pharmaceutical and dietetic fields.

4 Claims, 8 Drawing Sheets

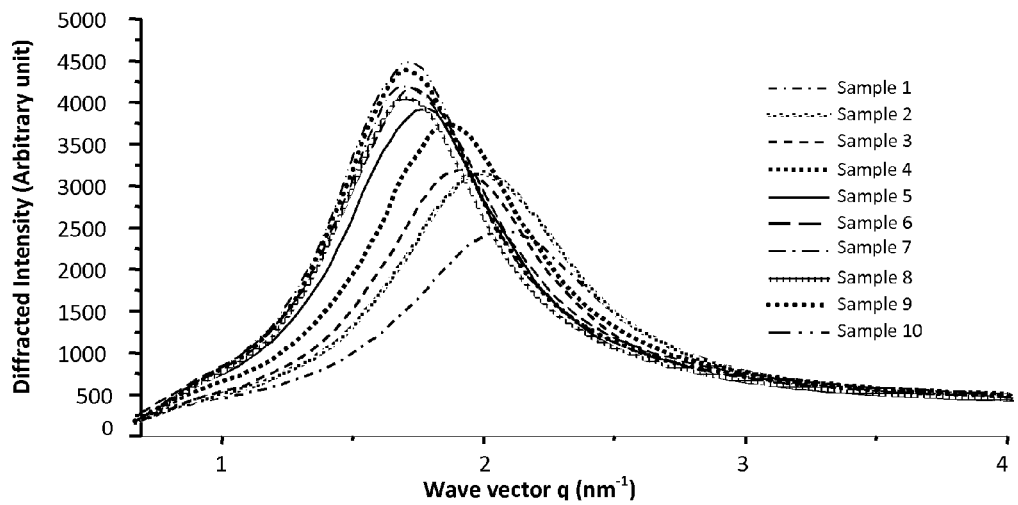
FIGURE 1a
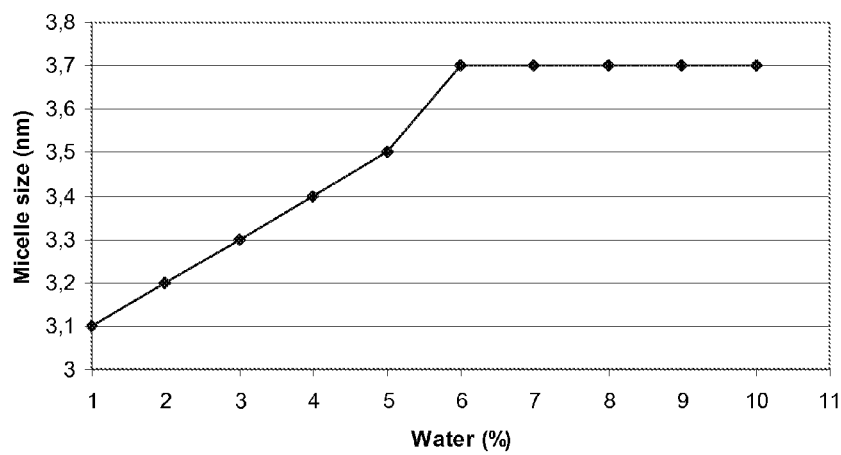
FIGURE 1b
FIGURE 1

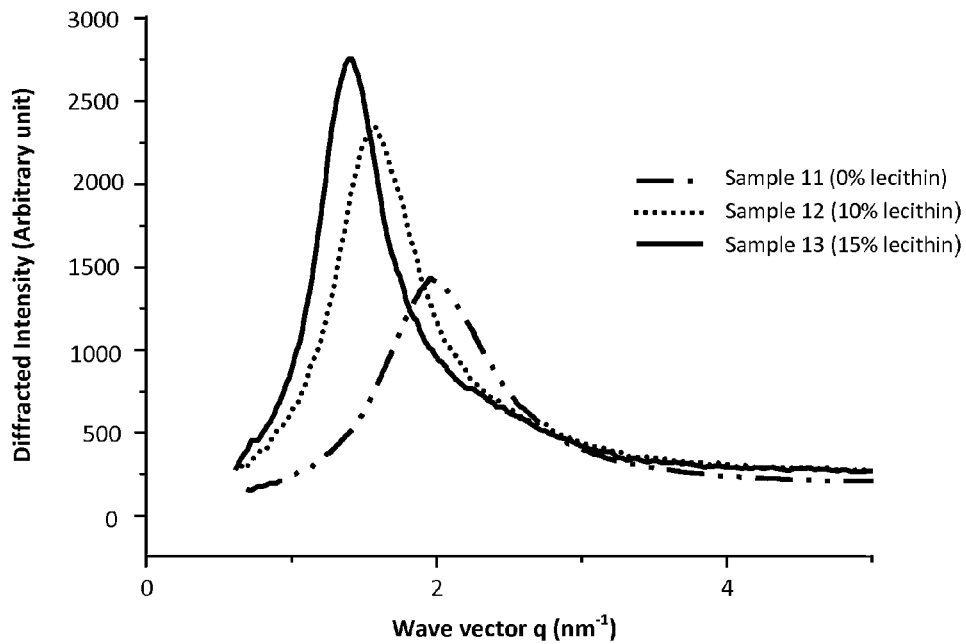
FIGURE 2a
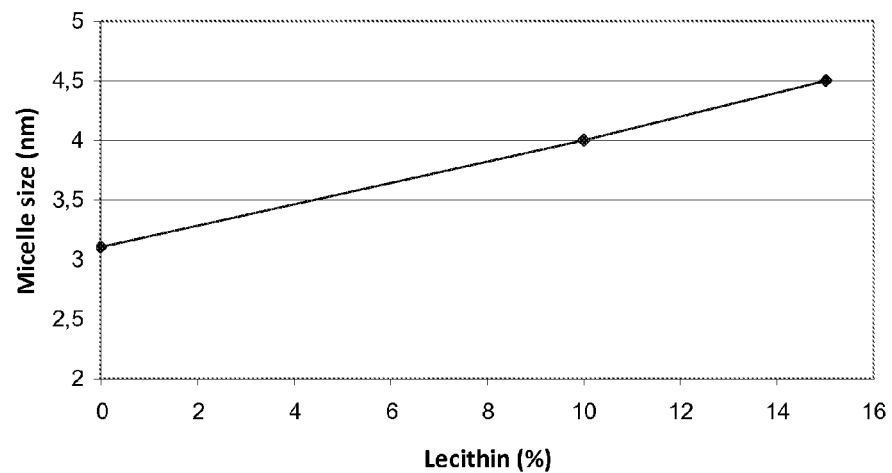
FIGURE 2b
FIGURE 2

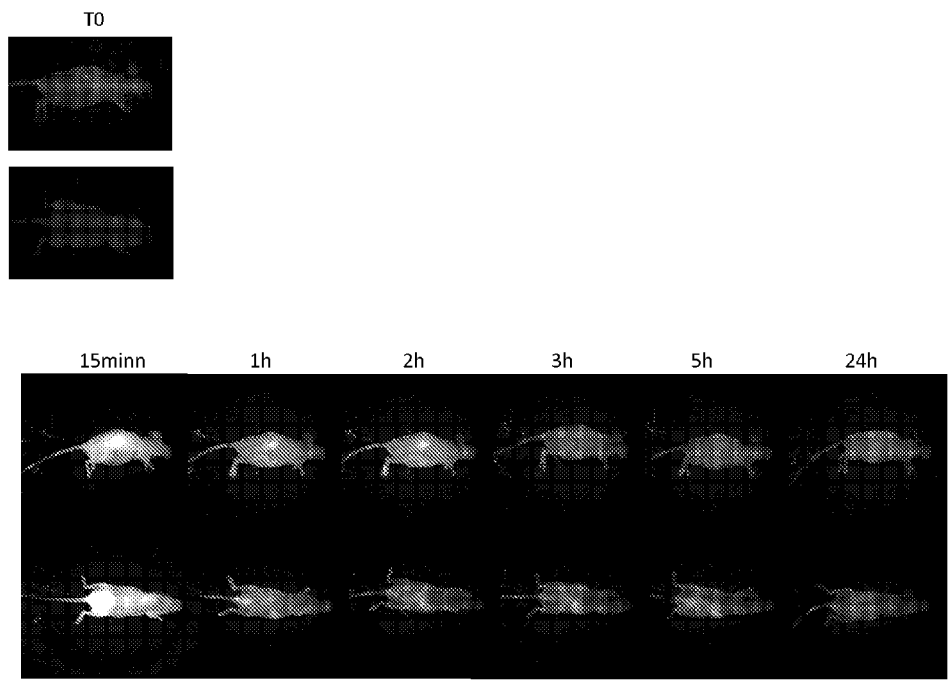
FIGURE 4a
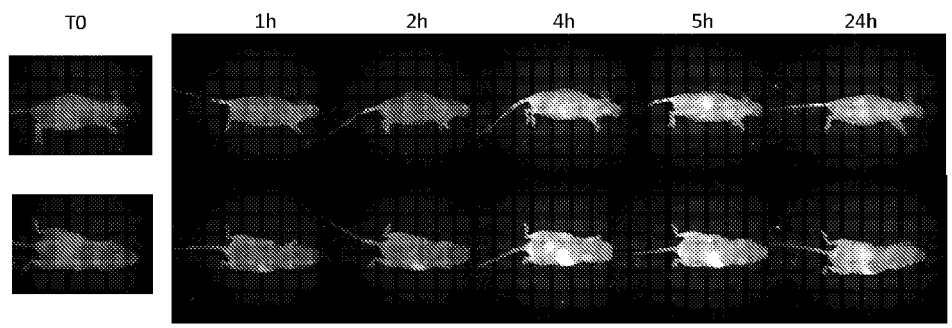
FIGURE 4b
FIGURE 4

REVERSE MICELLE SYSTEM COMPRISING NUCLEIC ACIDS AND USE THEREOF

CROSS-REFERENCE TO RELATED APPLICATIONS

This application is the U.S. national stage application of International Patent Application No. PCT/EP2011/054512, filed Mar. 24, 2011, which claims the benefit of U.S. Provisional Patent Application No. 61/317,050, filed Mar. 24, 2010.

FIELD OF THE INVENTION

The present invention relates to reverse micelle system based on sterols, acylglycerols, phospholipids or sphingolipids and nucleic acids. The reverse micelle system of the invention is able to cross mucosa and cellular membranes. It thus allows vectorization of nucleic acids to target sites. It is advantageously useful in the pharmaceutical and dietetic fields.

BACKGROUND OF THE INVENTION

RNAi (RNA interference) and antisense (AS) strategies consist in silencing the expression of a target gene by the use of nucleic acids which allow the degradation or the translational arrest of mRNA target. New antisense applications (exon skipping, alternative splicing correction), by masking the mutation responsible for an alternative splicing default, have permitted the synthesis of a functional protein. Aptamers are nucleic acids capable of interacting with a target protein and down regulating its synthesis. The discovery of all these nucleic acids, and more recently siRNA, miRNA and RNAa has opened wide perspectives in therapeutics for the treatment of diseases like genetic diseases, cancers, neurodegenerative diseases, infectious and inflammatory diseases or to block cell proliferation and diseases caused thereby.

However, these molecules are unstable in biological fluids, in vitro and in vivo, they display a poor intracellular penetration and low bioavailability. These critical drawbacks have limited their use in therapeutics. As a result, clinical applications of said nucleic acids have required chemical modifications with the aim of retaining their capacity to knockdown protein expression while increasing stability and cellular penetration. Research groups have also applied the nanotechnology approach to improve their delivery, to overcome most barriers that hampered the development of nucleic acids delivery based therapies. To improve bioavailability, many researchers have also attempted to use alternative administration routes: ocular, skin, oral, intramuscular. Those attempts have not been totally satisfactory so far. For instance, some of these attempts, more specifically assays with nucleic acids in liposome carriers have stimulated immune response.

The inventors have previously uncovered that complexes could be obtained from two organic compounds isolated from plant extracts and respectively constituted of sitosterol and acylglycerols and hydrosoluble therapeutic agents (WO2006/048772), these complexes being particularly effective agents as trans mucosal vectors of said therapeutic agents. Such vectorization of hydrosoluble therapeutic agents affords an important decrease of the administered amounts compared to their administration in the absence of micelles as previously described.

Said complexes have been shown effective to vectorize hydrosoluble therapeutic agents by mucosal immediate administration. The stability of microemulsions containing therapeutic agents is not however always satisfactory to allow their development as delivery systems for drugs and/or dietetic compounds for example. Such development requires formulations to be stable over longer periods of time, for instance over several weeks or months at room temperature.

It is an object of the present invention to overcome disadvantages of the prior art. There is an obvious need for a safe and efficient nucleic acids therapeutic strategy, and in particular for new tools that are able to achieve efficient gene expression modulation based therapy. More particularly, it is an object of the invention to provide a drug delivery system comprising a nucleic acid, in particular an oligonucleotide, which can be for instance administered mucosally, giving rise to a satisfactory drug bioavailability in an active form.

Incorporation of a phospholipid or a sphingolipid, in particular in specific amounts, in the formulation of microemulsions comprising high doses of nucleic acid surprisingly triggered an important increase in their stability.

The present invention describes new microemulsions formulations able to vectorize high quantities of nucleic acids, process of preparation and use thereof as delivery systems for drugs and/or dietetic compounds. "High" amounts refer here to amounts sufficient to obtain a therapeutic activity at the human scale, but that remain far lower than the amounts of nucleic acid delivered in absence of complexes.

This formulation advantageously renders possible the control and optimisation of the composition comprising micelles for their use in the pharmaceutical and dietetic fields.

SUMMARY OF THE INVENTION

The present invention relates to a delivery system for the release of a nucleic acid, preferably mucosally applied, as well as the compositions and methods for preparing the delivery system. Herein described are reverse micelle systems designed to reach this goal in a safe and controlled manner. The reverse micelle systems are able to be absorbed through mucosa and to vectorize nucleic acids under a protected form to any tissue of the organism.

More particularly, the present invention provides a reverse micelle transport system for dispensing a nucleic acid, in particular an oligonucleotide, capable of interaction with pre-mRNA, mRNA or protein, and modulation of gene expression. More specifically, reverse micelles according to the invention promote the absorption of the nucleic acid across mucosal epithelial barriers and allow the nucleic acid to be internalised into the target-cells. The reverse micelles of the invention comprise more specifically at least one nucleic acid, in particular an oligonucleotide, capable of modulating gene expression, a sterol, an acylglycerol, a phospholipid or a sphingolipid, an alcohol, and water.

The reverse micelles can be prepared according to a method described below using at least a sterol, an acylglycerol, a phospholipid or a sphingolipid, an alcohol and water.

Said micelles are more particularly obtainable by the following method:
  (a) Contacting (i) sterol, preferably sitosterol or cholesterol, (ii) acylglycerol, preferably diacylglycerol, (iii) phospholipid, preferably phosphatidylcholine, or sphingolipid (iv) alcohol, (v) water, preferably purified water, and (vi) at least a nucleic acid, in particular an oligonucleotide, capable of modulating gene expression,
  (b) Stirring mixture obtained in step (a), at 40° C. or less, and for a time sufficient to obtain formation of reverse micelles.

The parameters of stirring, for instance duration and speed of mechanical stirring, can be readily determined by any one skilled in the art and depend on experimental conditions. In practice, these parameters are such that a microemulsion is obtained; the speed is determined so as to enable formation of a visually limpid formulation, and duration of the stirring is such that the stirring may be stopped a few minutes after obtaining the visually limpid formulation.

The present invention further relates to a composition comprising reverse micelles of the invention and a pharmaceutically acceptable carrier, excipient or support.

DETAILED DESCRIPTION OF THE INVENTION

The following description is of preferred embodiments by way of examples only and without limitation to the combination of features necessary for implementing the invention.

Reverse Micelles

The reverse micelle system according to the invention is characterized as a microemulsion comprising a dispersion of water-nanodroplets in oil. The dispersion is stabilised by two surfactants (an acylglycerol, more preferably a diacylglycerol and a phospholipid, more preferably phosphatidylcholine, or a sphingolipid) and a co-surfactant (alcohol) that are most likely at the water/oil interface. The reverse micelles can be defined as a system wherein water forms the internal phase and the hydrophobic tails of the lipids form the continuous phase. Reverse micelles containing oil(s), surfactant(s), co-surfactant(s), and an aqueous phase are also characterized as water-in-oil microemulsions. These microemulsions are thermodynamically stable and visually limpid.

Generally, the size of micelles according to the invention is very small, more particularly, it is less than 10 nm; more specifically it is less than 8 nm and more preferably less than 6 nm. The size may vary with the quantity of added water and phospholipid or sphingolipid. The present invention relates more particularly to reverse micelles with an aqueous core of around 4 nm, preferably 3 to 5 nm, more preferably from 3.5 to 5 nm, in particular from 3.7 to 4.5 nm.

The reverse micelles and the size of their aqueous core can be characterized by various methods, including:

Small Angle X-Ray Scattering (SAXS)
Neutrons Scattering
Transmission Electron Microscopy (TEM)
Dynamic Light Scattering (DLS)

The ratios of the lipidic constituents (including sterol, acylglycerol and phospholipid or sphingolipid) in the reverse micelle system according to the invention can vary. For instance, the weight ratio sterol/acylglycerol can range from 0.015 to 0.05, more particularly from 0.03 to 0.04.

The weight ratio phospholipid or sphingolipid/acylglycerol can range from 0.05 to 0.40, in particular from 0.06 to 0.25. The weight of phospholipid or sphingolipid respectively corresponds to the total weight of the mixture of phospholipids or sphingolipids, for instance the weight of lecithin, used in the formulation. Similarly, the weight of acylgylycerol corresponds to the total weight of the mixture usually containing an acylglycerol, or a mixture of acylglycerols, with glycerol and fatty acids derived from said acylglycerol(s).

The compounds of the reverse micelle system can be analyzed by appropriate means. More specifically, sterols can be identified by gas chromatographic analysis and acylglycerol by high-performance liquid chromatography (HPLC), in particular with a light scattering detector, on a silica column, in the presence of an eluent, e.g. isocratic acetonitrile. Gas chromatography can also be used to analyze diacylglycerols. Phospholipids and sphingolipids can be analyzed by high-performance liquid chromatography (HPLC), with a diol column with a light scattering detector.

Reverse micelles are dynamic systems. Brownian motion causes perpetual collisions of micelles, which lead to coalescence of micelles and exchange of the aqueous cores. Separation and regeneration of micelles occur and allow chemical reactions between different solutions. The exchange rate between micelles increases in particular with temperature, the length of hydrocarbon chains of the surfactant, and the water/surfactant ratio. Within the context of the invention, aqueous cores of micelles must have a specific size allowing one or more molecules of nucleic acid, in particular oligonucleotide, capable of modulating gene expression, to be stabilised in the prepared micelles. As mentioned above, the size of the aqueous core is preferably around 4 nm, more preferably from 3 to 5 nm, more specifically from 3.5 to 5 nm, in particular from 3.7 to 4.5 nm.

Reverse micelles may exist in the system of the invention as different structural organizations, such as spheres, cylinders or branched cylinders for instance.

Without being bound to any theory, it seems that inclusion of a phospholipid or a sphingolipid in the reverse micelle system allows formation of stable micelles with greater diameter and volume, thus allowing vectorization of greater quantities of nucleic acid. This increase in vectorized nucleic acid amounts affords vectorization of sufficient amounts to obtain a therapeutic activity. The incorporation of the phospholipid or sphingolipid in the reverse micelle system further confers a higher stability of the microemulsions, in particular of the microemulsions containing high quantities of nucleic acid.

The reverse micelles system of the invention ensures absorption of the compounds to be delivered across mucosa, preferably across mouth, nasal and/or rectal mucosa, more preferably across mouth mucosa. Also, reverse micelles of the present invention provide an important bioavailability with low variability of absorption.

Method for Preparing Reverse Micelles

In a particular embodiment, the invention relates to a method for preparing reverse micelles presenting an aqueous core of around 4 nm, preferably from 3 to 5 nm, more preferably from 3.5 to 5 nm, in particular from 3.7 to 4.5 nm and involving at least one nucleic acid, in particular an oligonucleotide, capable of modulating gene expression, a sterol, an acylglycerol, a phospholipid or a sphingolipid, an alcohol, and water, wherein said method comprises the following steps:

(a) Contacting (i) sterol, (ii) acylglycerol, preferably diacylglycerol, (iii) phospholipid, preferably phosphatidylcholine, or sphingolipid, (iv) alcohol, (v) water, preferably purified water, and (vi) at least a nucleic acid, in particular an oligonucleotide, capable of modulating gene expression, (b) Stirring mixture obtained in step (a), at 40° C. or less, and for a time sufficient to obtain formation of reverse micelles.

The obtained and recovered reverse micelles are then particularly useful as a delivery system for nucleic acids. Step (b) of the process is of particular importance since it allows reverse micelles to be obtained, said reverse micelles being then useful as a transport system for delivering the nucleic acid into the target sites. Target sites may for instance be cells of a specific tissue.

In a particular embodiment, the nucleic acid is first solubilised in water (preferably purified water) to form an aqueous mixture. Said aqueous mixture is then introduced into the oily mixture (step(a)). The oily mixture preferably comprises at least a sterol, an acylglycerol, a phospholipid or a sphingolipid, and an alcohol.

The compounds involved in step (a) will be described in more details below.

Stirring of the mixture obtained by step (a) is carried out at a temperature less than or equal to 40° C., specifically ranging from 15° C. to 40° C., or more preferably from 25° C. to 40° C., or more specifically from 30° C. to 37° C. The time sufficient can vary in particular upon the used stirring technique. The time of stirring is anyhow the time needed to convert the initial mixture into a visually limpid reverse micelle solution.

One skilled in the art knows how to select excipients or components that may be used along with the composition according to the present invention in order to keep their beneficial properties. In particular, the presence of glycerol can, when introduced in large amount, prevent the formation of reverse micelles or break the reverse micelle system. More specifically, no more than 2.5% (percent expressed by weight of glycerol/weight of acylglycerol) is used for the preparation of the reverse micelles of the present invention.

Other compounds can be introduced in step (a). One can cite for instance colouring agents and/or flavouring substances.

In an advantageous manner, the compounds cited above or the commercially available mixtures containing them are the only ingredients introduced to prepare the micelle system and consequently the only ones present in the micelle system of the invention.

Stirring of step (b) may for instance be performed by mechanical stirring.

The common materials may be propellers whose fast movements generate turbulences and swirls allowing interpenetration of particles and formation of reverse micelles within the mixture.

Mechanical stirring speed is preferably ranging from 100 to 2,000 r/minute, more preferably from 300 to 700 r/minute. The implemented volumes, device, and stirring speed depend on and should be adapted with the reactants and amounts thereof.

Temperature is more specifically ranging from 15° C. to 40° C., or from 25° C. to 40° C., or even more specifically from 30° C. to 37° C.

Reverse Micelles Compounds
Acylglycerol

Acylglycerols useful for the preparation of the reverse micelle system according to the invention can be isolated from the majority of animals and more preferably plants.

Acylglycerols include mono-, di and triacylglycerols. In a particular embodiment, acylglycerols preferentially used in the present invention present the following formula (I):

in which:
R$_1$ is an acyl residue of a linear or branched, saturated or unsaturated fatty acid having between 14 and 24 carbon atoms, a hydrogen atom, or a mono-, di- or tri-galactose or glucose;
R$_2$ is an acyl residue of a linear or branched, saturated or unsaturated fatty acid having between 2 and 18 carbon atoms;
R$_3$ is an acyl residue of a linear or branched, saturated or unsaturated fatty acid having between 14 and 24 carbon atoms, or a hydrogen atom.

According to a particular embodiment, R$_1$ or R$_3$, preferably only one of R$_1$ and R$_3$, in particular only R$_1$, represents an acyl residue of oleic acid (C18: 1[cis]-9).

According to a particular aspect, R$_2$ has one unsaturated bond (e.g; ethylenic bond) and has advantageously 18 carbon atoms, preferably R$_2$ is an oleic acid residue (oleoyl group), one of its positional isomers with respect to the double bond (cis-6,7,9,11 and 13) or one of its iso-branched isomers.

According to another particular aspect, R$_1$ represents an oleoyl group.

According to another particular aspect, R$_2$ represents an acetyl group.

According to another particular aspect, R$_3$ is a hydrogen atom.

As a general rule, oil containing a high concentration of oleic acid will be chosen as a useful source of acylglycerols according to the invention. Such oil usually contains a high proportion of acylglycerols useful according to the invention.

According to a particular aspect of the invention, the preferred diacylglycerols are selected in the group consisting of 1,2-dioleoylglycerol (or also named herein 1,2-diolein) and 1-oleoyl-2-acetyl glycerol.

A certain number of them, and more particularly those which are found to be the most active in the applications sought after, are also available commercially. This is the case particularly for 1-oleoyl-2-acetylglycerol and 1,2-dioleoylglycerol. Glycerol monooleate 40 contains about 33% of dioleoylglycerol, and about 11% of 1,2-diolein and is pharmaceutically accepted (European Pharmacopeia (4$^{th}$ Edition), USP 25/NF20, and Japanese Standard of food Additives). Such product is for instance commercially available by Gattefosse Company under the name PECEOL®.

The acylglycerols are preferably incorporated or comprised in the composition or reverse micelle system in an amount by weight ranging from 50 g to 90 g with respect to 100 g of the total weight of the composition or reverse micelle system according to the invention. The amounts specified herein will be adapted with respect to the other compounds as to correspond more specifically to the weight ratios identified below.

Sterols

The sterols useful for the preparation of the reverse micelle system according to the invention are preferably natural sterols, such as cholesterol or phytosterols (vegetable sterols). Sitosterol and cholesterol are the preferred sterols useful for the reverse micelle system according to the invention.

Sitosterol and cholesterol are commercially available. More particularly, commercial sitosterol which is extracted from soya can be used. In such a product, the sitosterol generally represents from 50 to 80% by weight of the product and is generally found in a mixture with campesterol and sitostanol in respective proportions in the order of 15% each. Commercial sitosterol which is extracted from a variety of pine called tall oil can also be used. In general, it will be possible to use sitosterol in mixture with sitostanol. Preferably, said mixture comprises at least 50% sitosterol by weight of the mixture.

As mentioned above, the ratios of the lipidic constituents (sterols, acylglycerol and phospholipids or sphingolipids) in the reverse micelle system according to the invention can vary. Preferably, the weight ratio sterol/acylglycerol can range from 0.015 to 0.05, more particularly from 0.03 to 0.04.

The weight of sterol corresponds in the present invention to the total weight of sterols used in the formulation, for instance the weight of phytosterol.

The sterols are preferably incorporated or comprised in the composition or reverse micelle system in an amount by weight ranging from 0.825 g to 4.5 g with respect to 100 g of the total weight of the composition or reverse micelle system according to the invention. The amounts specified herein will be adapted with respect to the other compounds as to correspond more specifically to the weight ratios identified above and/or below.

Phospholipids and Sphingolipids

Phospholipids are formed of a glycerol linked to 2 fatty acids and to a phosphate group. The variability of phospholipids relies on the fatty acids that are attached to the glycerol and on the chemical groups that are susceptible to link to the phosphate group. Phospholipids are, with sphingolipids, the major lipidic constituents of biological membranes.

Among phospholipids useful in the present invention may be cited phosphatidylethanolamine, phosphatidylserine, phosphatidylglycerol, diphosphatidylglycerol, phosphatidylinositol, and phosphatidylcholine.

In a particular embodiment, the phospholipid is phosphatidylcholine. Phosphatidylcholine is also known as 1,2-diacyl-glycero-3-phosphocholine or PtdCho.

Phosphatidylcholine is formed from a choline, a phosphate group, a glycerol and two fatty acids. It is actually a group of molecules, wherein the fatty acid compositions varies from one molecule to another. Phosphatidylcholine may be obtained from commercial lecithin that contains phosphatidylcholine in weight concentrations of 20 to 98%. The lecithin preferably used for the preparation of the reverse micelles according to the invention is Epikuron 200® and contains phosphatidylcholine at a concentration of more than 90%.

Sphingolipids are a class of lipids derived from the aliphatic amino alcohol sphingosine. Among sphingolipids that may be used in the present invention may be cited acylsphingosine, sphingomyelins, glycosphingolipids, and gangliosides.

The reverse micelles system of the invention may comprise phospholipids, sphingolipids, or a mixture of both types of compounds, preferably phospholipids.

According to a specific embodiment, the reverse micelles system of the invention comprises phospholipids.

The weight ratio phospholipid and/or sphingolipid/acylglycerol in compositions or reverse micelle systems according to the invention is from 0.05 to 0.40, preferably from 0.06 to 0.25.

The phospholipids or sphingolipids are preferably incorporated or comprised in the composition or reverse micelle system in an amount by weight ranging from 1 g to 30 g, preferably from 5 to 20 g, with respect to 100 g of the total weight of the composition or reverse micelle system according to the invention. The amounts specified herein will be adapted with respect to the other compounds as to correspond more specifically to the weight ratios identified above.

Alcohols

The alcohols useful for the preparation of the reverse-micelle system according to the invention are preferably linear or branched mono-alcohols from C2 to C6. Examples of alcohols are ethanol, 1-butanol, 2-butanol, 3-methyl-1-butanol, 2-methyl-1-propanol, 1-pentanol, 1-propanol, 2-propanol and any mixture thereof. In a particular embodiment of the invention, alcohol is ethanol.

The alcohol is preferably incorporated or comprised in the composition or reverse micelle system in an amount by weight ranging from 5 g to 12 g with respect to 100 g of the total weight of the composition or reverse micelle system according to the invention.

Water

The water useful for the preparation of the reverse-micelle system according to the invention is preferably purified water, more preferably RNAse or DNAse-free water.

Water is preferably incorporated or comprised in the composition or reverse micelle systems in an amount by weight ranging from 1 g to 15 g, preferably from 5 g to 15 g, with respect to 100 ml of the total volume of the composition or reverse micelle system according to the invention.

One of ordinary skill in the art will adapt the amount of phospholipid or sphingolipid in the systems to the desired amount of water. For instance, increasing amount of water should imply increasing amount of phospholipid or sphingolipid in the systems.

Nucleic Acids

In the present invention, the term "nucleic acid" refers to any nucleic acid capable of interacting with mRNA, pre-mRNA or protein and capable of modulating gene expression. Preferred nucleic acids are able to up or down regulate the expression of target protein(s).

"Nucleic acid" includes any DNA (deoxyribonucleic acid) and RNA (ribonucleic acid). The terms include single-stranded RNA, single-stranded DNA, double-stranded RNA, double-stranded DNA, plasmid DNA, isolated RNA such as partially purified RNA, essentially pure RNA, synthetic RNA, recombinantly produced RNA, aptamers, as well as nucleic acids comprising non-standard nucleotides, such as non-naturally occurring nucleotides or chemically synthesized nucleotides or deoxynucleotides. One can cite for instance gapmers.

By "oligonucleotide" is meant a nucleic acid comprising from 5 to 100 nucleotides, preferably from 10 to 90 nucleotides, more preferably from 13 to 80 nucleotides, more particularly from 13 to 25 nucleotides.

The terms "antisense oligonucleotides", "short interfering nucleic acid" (siNA), "short interfering RNA" (siRNA), "short interfering nucleic acid molecule", "short interfering oligonucleotide molecule", "miRNA", "micro RNA", "RNA activation" (RNAa), "short hairpin RNA" (shRNA), and "aptamers", as used herein, refer to any nucleic acid molecule capable of modulating gene expression by up or down regulating (for instance gene silencing) target protein expression in a sequence-specific manner. The various nucleic acid strategies to modulate gene expression are described below.

1. RNA Interference Strategy

RNA interference (RNAi) describes a process wherein double-stranded RNA (dsRNA), when present inside a cell, inhibits expression of an endogenous gene that has an identical or nearly identical sequence to that of the dsRNA (double stranded RNA). Inhibition is caused by the specific degradation of the messenger RNA (mRNA) transcribed from the target gene. In greater detail, RNA interference describes a process of sequence-specific post-transcriptional gene silencing in animals mediated by the expression of "short interfering RNAs" (siRNAs) after in situ cleavage (Brummelkamp T. R. and al, 2002). The initial basic process involves dsRNA that is/are processed by cleavage into shorter units (the so called siRNA) that guide recognition and targeted cleavage of homologous target messenger RNA (mRNA).

Accordingly, the method does not require time-consuming genetic manipulations as those needed for classical gene knock-out strategies and has therefore emerged as a valuable tool in molecular genetics that may also be applied to human therapy.

The currently known mechanism of RNAi can be described as follows:

The processing of dsRNA into siRNAs, which in turn induces degradation of the intended target mRNA, is a two-step RNA degradation process. The first step involves a dsRNA endonuclease (ribonuclease III-like; RNase III-like) activity that processes dsRNA into smaller sense and anti-sense RNAs which are most often in the range of 19 to 25 nucleotides (nt) long, giving rise to the so called short interfering RNAs (siRNAs). This RNase III-type protein is termed "Dicer". In a second step, the antisense siRNAs produced combine with, and serve as guides for, a different ribonuclease complex called RNA-induced silencing complex (RISC), which allows annealing of the siRNA and the homologous single-stranded target mRNA, and the cleavage of the target homologous single-stranded mRNAs. Cleavage of the target mRNA has been observed to place in the middle of the duplex region complementary to the antisense strand of the siRNA duplex and the intended target mRNA (Dykxhoorn D. M. and al, 2003).

A siRNA alternative is a plasmid coding for hairpin siRNA, which is called shRNA strategy (small hairpin RNA). In the cell, hairpin RNA is generated and interacts with the DICER protein, resulting in a functional siRNA which will be incorporated in the RISC complex and acting like a classical siRNA (Wacheck V. and Zangemeister-Wittke U., 2006). The transfection with such plasmids allows numerous copies of shRNA and of endogenous siRNA molecules (McCaffrey A. P. and al, 2002).

Micro RNAs (miRNAs) are non coding RNAs of 21 to 25 nucleotides, controlling genes expression at post-transcriptional level. miRNAs are synthesized from RNA polymerase II or RNA polymerase III in a pre-miRNA of 125 nucleotides. Pre-miRNA are cleaved in the nucleus by the enzyme Drosha, giving rise to a precursor called imperfect duplex hairpin RNA (or miRNA-based hairpin RNA). These imperfect duplex hairpin RNAs are exported from the nucleus to the cytoplasm by exportin-5 protein, where it is cleaved by the enzyme DICER, giving rise to mature miRNAs. miRNAs combine with RISC complex which allows total or partial annealing with the homologous single-stranded target mRNA. Partial annealing with the mRNA leads to the repression of protein translation, whereas total annealing leads to cleavage of the single-stranded mRNA (Dykxhoorn D. M. and al, 2003 for review).

By "antisense strand" is meant a nucleotide sequence of a siRNA molecule having complementarity to a sense region of the siRNA molecule. In addition, the antisense strand of a siRNA molecule comprises a nucleic acid sequence having homology with a target nucleic acid sequence.

By "sense strand" is meant a nucleotide sequence of a siRNA molecule having complementarity to an antisense region of the siRNA molecule.

By "modulate" and "modulation" is meant that the expression of the gene, or level of RNA molecule or equivalent RNA molecules encoding one or more proteins or protein subunits, or activity of one or more proteins or protein subunits is up regulated or down regulated, such that expression, level, or activity is greater than or less than that observed in the absence of the modulator. Within the scope of the invention, the preferred form of modulation is inhibition, but the use of the word "modulate" is not limited to this definition.

By "inhibit", "silence" or "down regulate" it is meant that the levels of expression product or level of RNAs or equivalent RNAs encoding one or more gene products is reduced below that observed in the absence of the nucleic acid molecule of the invention. In one embodiment, inhibition with a nucleic acid molecule capable of mediating RNA interference (siRNA, shRNA, miRNA) preferably is below that level observed in the presence of an inactive or attenuated molecule that is unable to mediate an RNAi response.

By "target protein" is meant any protein whose expression or activity is to be modulated.

By "target nucleic acid" or "target gene" is meant any nucleic acid sequence whose expression or activity is to be modulated. The target nucleic acid can be for instance DNA or RNA.

The nucleic acid capable of modulating gene expression includes, but is not limited to, "short interfering nucleic acid" (siNA), "short interfering RNA" (siRNA), "short interfering nucleic acid molecule", "short interfering oligonucleotide molecule", "miRNA", "micro RNA" and "short hairpin RNA" (shRNA), as defined above.

2. Antisense Strategy.

a. Classical Antisense Strategy.

Antisense strategy is a special and rational strategy based on the oligonucleotide chemical modification and which purpose is to inhibit specifically gene expression, with antisense oligonucleotides (ASON) complementary of the target RNA sequence, resulting in an inhibition of the protein expression. ASON are considered since 1978 as a new class of drugs capable of silencing specifically genes implicated in diseases (Gallo M. and al, 2003, Chan J. H. and al, 2006).

ASON is a single-stranded deoxyribonucleotide (DNA) or ribonucleotide (RNA) of 13 to 25, preferably 15 to 21, bases. Hybridization of the ASON on the target mRNA leads to the translation stop by steric-blocking, to its destruction by recruitment of the intracellular RNase H, which role is to cleave the DNA/RNA duplex, or to destabilize the pre-mRNA, resulting in a splicing inhibition (Kurreck J., 2003; Chan J. H. and al, 2006).

b. New Applications for Antisense Oligonucleotides.

In several recent applications, the ASON is not used to inhibit a gene expression, but on the contrary to restore a normal protein synthesis. In alternative splicing correction and exon skipping models, the alternative splicing is abnormal. In general, an aberrant mutation located at an intron (splicing correction) or exon (exon skipping) locus, is at the origin of an abnormal splicing, resulting in a non-functional protein responsible for the disease symptoms (Kang S. H. and al, 1998; Sazani P. and Kole R., 2003).

ASON is capable to hybridize specifically at the mutation locus, in a sequence-dependant manner, masking the mutation and reorienting the machinery towards a normal alternative splicing with the expression of the functional protein.

These applications have a huge interest in the treatment of several cancers, neurologic diseases such as Huntington's disease, age related macular disease and genetic diseases such as β-Thalassemia, Duchenne Muscular Distrophy (DMD), Hutchinson Gilford Progeria Syndrome (HGPS) or Cystic Fibrosis (CF) for the CFTR mutation (Mercatante D. R. and al, 2001; Srebrow A and Kornblihtt A. R. 2006; Brinkman B. M., 2004, and Venables J. P., 2006).

c. Chemical Modifications and New Generations of Antisense Oligonucleotides.

Efforts have been realised to modify chemical ASON structure, so that the RNase H could not degrade the duplexes of nucleic acids during the hybridation of the ASON on the RNA strand: structural modifications at the ribose level (2'-fluoro, 2'-methyl, 2'-methoxy), at the base level and at the backbone level (phosphodiester, phosphorithioate).

ASON with chemical modification structure of the second (2'-O-methyl, 2'-O-methoxyethyl or MOE) and third (locked nucleic acid or LNA, peptide nucleic acid or PNA, phosphoamidate morpholino or PMO) generation, not activator of the RNase H enzyme, are preferred (Altmann K. H. and al, 1996, Egholm M. and al, 1993; Singh S. K. and al, 1998, Summerton J. and Weller D., 1997).

Gapmers are chimeric antisense oligomers (mix of RNA and DNA nucleotides) with a short strech of phosphorothioate DNA (5-12 nucleotides). They have been used to obtain RNAse H mediated cleavage of target RNA and mRNA degradation. In addition to high ASO potency, they improve target accessibility and nuclease resistance (Kurreck J., 2003).

By "antisense oligonucleotide" is meant a single-stranded oligonucleotide capable of specific hybridization with the mRNA (in the cell cytoplasm) or the pre-mRNA (in the cell nucleus).

The nucleic acid capable of mediating antisense mechanism includes, but is not limited to, single-stranded DNA oligonucleotides, single-stranded RNA oligonucleotides, unmodified and chemically modified oligonucleotides.

3. Aptamers.

Aptamers are 20 to 80 nucleotides nucleic acids, composed of DNA, RNA or chemically modified nucleotides (2'-fluoro, 2'-O-methyl or phosphorothioate) (Chan J. H. and al, 2006). Thanks to their 3D structure, aptamers are able to bind to various molecules and proteins with a high affinity, via Van der Walls, hydrogen and electrostatic bounds (Pendergrast P. S. and al, 2005).

The most interested application of aptamers appears to be regulation of gene expression by inhibiting protein activity.

High affinity aptamers can be obtained by the SELEX technology (Systematic Evolution of Ligands by Exponential Enrichment), developed in 1990. A pool of oligonucleotides ($10^{13}$ to $10^{15}$ different sequences) is mixed with the target and only those linked to the target are selected. These aptamers are then amplified and used in the following cycle. After 5 to 15 amplifications steps, high affinity aptamers are obtained (Rimmelle M., 2003; Chauveau F. and al, 2006). This technique is now robotized.

Due to their lack of immunogenicity, aptamers seem to be good candidates for therapeutic applications in autoimmune diseases (White R. R. and al, 2000; Kim Y. M. and al, 2003; Drolet D. W. and al, 2000 and Rhodes A. and al, 2000).

Such agents incorporated in the reverse micelle system according to the invention can cross mucosal epithelial barriers and present thereby its therapeutic effect at the target sites.

The nucleic acids capable of modulating gene expression are present in the aqueous core of the reverse micelles.

Stability and activity of the therapeutic agent can be controlled essentially by water concentration in the mixture.

The amount of the nucleic acid capable of modulating gene expression incorporated into the reverse micelle system is determined by their solubility in the hydrophilic phase (aqueous core). Preferably, the amount of therapeutic agent included in the reverse micelle system depends on the size of the nucleic acid capable of modulating gene expression.

In the present invention, the weight concentration of the nucleic acid in the microemulsion is more specifically calculated with a density of 0.94+/−0.03 for the microemulsion.

The density is generally measured at room temperature and atmospheric pressure.

Reverse Micelle System and Use Thereof

The reverse micelles of the invention allow the nucleic acid included therein to be administered and transported to cells with a high degree of protection, in particular without affecting its stability.

It is known today that a reverse micelle system can be used for the preparation of nanomaterials, which act as micro reactors. The activity and stability of bio molecules can be controlled, mainly by the concentration of water in the reverse micelle system.

An object of the invention concerns a pharmaceutical composition comprising reverse micelles as defined above and at least a pharmaceutically acceptable carrier, excipient or support.

According to a specific embodiment, the pharmaceutical composition according to the invention comprises from 5 to 20 g of phospholipid or sphingolipid with respect to 100 g of composition, and from 5 to 15 g of water with respect to 100 ml of composition.

According to a particular embodiment, the pharmaceutical composition is in the form of a capsule, a caplet, an aerosol, a spray, a solution or a soft elastic gelatin capsule. A further object of the invention concerns the use of reverse micelles as defined above for preparing a pharmaceutical composition intended for the delivery, more specifically the mucosal delivery, of one or more nucleic acids. The pharmaceutical composition is more particularly intended to prevent, treat, and/or improve the symptoms of genetic diseases, cancers, neurodegenerative diseases, infectious and/or inflammatory diseases, diseases or disorders due to cell proliferation.

Another object of the invention concerns a method for the delivery of one or more nucleic acids to a mammal (in particular human), said method comprising administering the reverse micelle composition as defined above to the mammal. In a specific embodiment, the present invention provides a method for the mucosal delivery of one or more nucleic acids, said method comprising mucosally administering to said mammal (in particular human) a reverse micelle composition as defined above.

The present invention provides a method for the prevention, treatment, and/or improvement of the symptoms of a genetic disease, cancer, neurodegenerative disease, infectious and inflammatory disease or a disease due to cell proliferation, said method comprising administering to said human in need thereof an effective amount of a reverse micelle composition as defined above and comprising one or more nucleic acids useful in the prevention, treatment or improvement of the symptoms of the genetic disease, cancer, neurodegenerative disease, infectious and inflammatory disease or disease due to cell proliferation. In a specific embodiment, the present invention provides a method for the prevention, treatment or improvement of one or more symptoms associated with a disease or disorder as defined above, said method comprising mucosally administering to a subject in need thereof an effective amount of a reverse micelle composition as defined above and comprising one or more nucleic acids useful in the prevention, treatment or improvement of one or more symptoms associated with said disease or disorder.

As pharmaceutically acceptable excipient, vehicle or carrier, any excipient, vehicle or carrier well-known to the person skilled in the art may be used. Other additives well-known to the person skilled in the art such as stabilisers, drying agents, binders or pH buffers may also be used. Preferred excipients in accordance with the invention promote adherence of the finished product to the mucosa.

The present invention further concerns the use of a pharmaceutical composition as described above for the delivery of at least a nucleic acid to a mammal, said delivery comprising mucosal administration of the pharmaceutical composition.

In a specific embodiment, the pharmaceutical composition of the invention is used for the delivery, more specifically the mucosal delivery, of at least a nucleic acid.

Nucleic acids in reverse micelle system formulated according to the invention are preferably able to cross the blood brain barrier. Consequently, they can be useful in the treatment of central nervous system (CNS) disorders, in particular genetic, tumoral, viral and/or degenerative diseases in the CNS.

The compositions of the invention can be administered in different ways, in particular via mucosal tissue absorption, with a buccal, nasal, vaginal or digestive absorption.

"Subject" refers to an organism to which the nucleic acid of the invention can be administered. The subject may be a non-human animal, preferably a mammal. The preferred subject is a human subject.

As used herein, the terms "mucosa" and "mucosal" refer to a mucous tissue such as of the respiratory, digestive, or genital tissue. "Mucosal delivery", "mucosal administration" and analogous terms as used herein refer to the administration of a composition through a mucosal tissue. "Mucosal delivery", "mucosal administration" and analogous terms include, but are not limited to, the delivery of a composition through bronchi, gingival, lingual, nasal, oral, vaginal, rectal, and gastro-intestinal mucosal tissue.

In a preferred embodiment of the invention, the reverse micelle composition of the invention is mucosally administered as a capsule, a caplet, an aerosol, a spray, a solution, or a soft elastic gelatin capsule. The compositions of the invention can for instance be introduced in liquid form into capsules which release their contents in the mouth or on any mucous tissue. Preferably, the reverse micelle compositions of the invention are administered to a mammal, more preferably a human, to treat a disease or disorder, such as a genetic disease, cancer, neurodegenerative disease, infectious and inflammatory disease or a disease due to cell proliferation.

The following examples are intended to exemplify the operation of the present invention but not to limit its scope.

DESCRIPTION OF THE FIGURES

FIG. 1: Evaluation of the impact of the rate of incorporated water in absence of lecithin on diffraction curves (FIG. 1a) and size (FIG. 1b) of reverse micelles.

FIG. 2: Evaluation of the impact of the rate of incorporated water in presence of lecithin on diffraction curves (FIG. 2a) and size (FIG. 2b) of reverse micelles.

FIG. 4: In vivo biodistribution of naked Alexa 700-ClB1 siRNA (FIG. 4a) and Alexa 700-ClB1 siRNA formulated in reverse micelles (FIG. 4b).

EXAMPLES

Example 1

Figure 3:
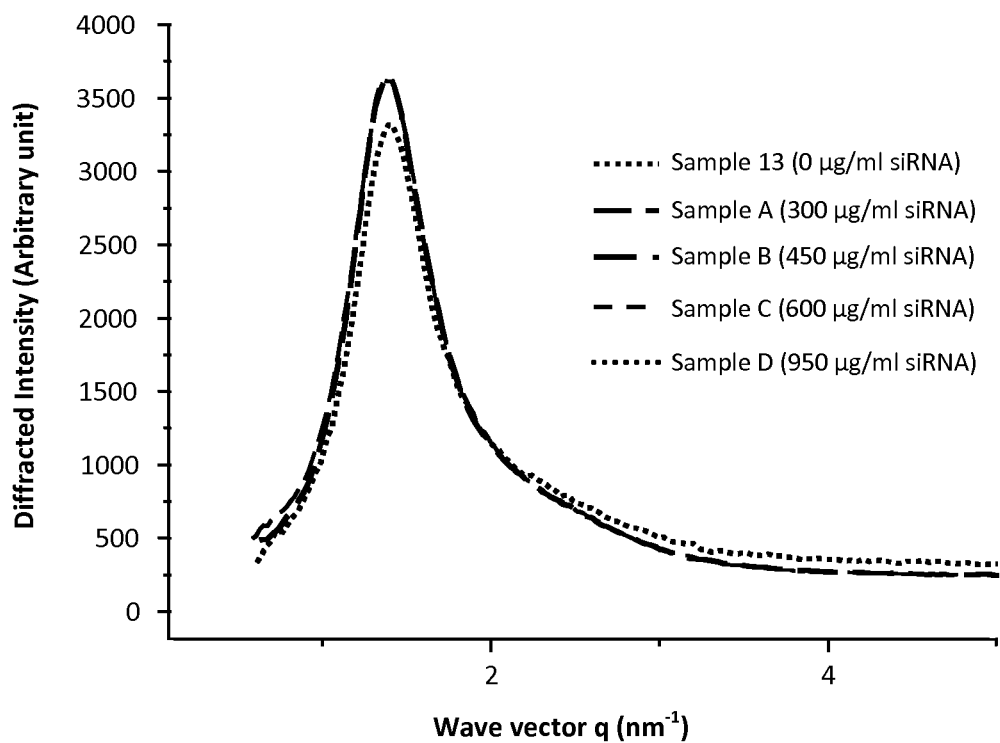
FIG. 3: Evaluation of the impact of incorporated GAPDH siRNA content on diffraction curves of reverse micelles.

Evaluation of Water Incorporation Impact on Formation and Size of Reverse Micelles in Absence of Lecithin The aim of this study was to evaluate by X ray diffraction method and visual determination the impact of water content on the formation of thermodynamically stable microemulsions and the size of reverse micelles dispersed therein.

10 formulations of reverse micelles with different percentages of water were prepared according to the procedure below.

0.7 g of phytosterol were dissolved in 1.4 g of absolute ethanol by magnetic stirring at 300 r/min for 15 minutes at 37° C. Glycerol monooleate was added thereto and magnetic stirring was carried out at 500 r/min for 45 minutes at 37° C. Purified water was added to this oil mixture and stirred between 300 and 500 r/min for 60 minutes at 37° C. to form "empty" reverse micelles.

The different formulations are summarized in the table below.

| Sample | Water content (%) | Glycerol monooleate | Water |
|---|---|---|---|
| 1 | 1 | 25.8 g | 0.3 g |
| 2 | 2 | 25.5 g | 0.6 g |
| 3 | 3 | 25.2 g | 0.9 g |
| 4 | 4 | 24.9 g | 1.2 g |
| 5 | 5 | 24.6 g | 1.5 g |
| 6 | 6 | 24.3 g | 1.8 g |
| 7 | 7 | 24.0 g | 2.1 g |
| 8 | 8 | 23.7 g | 2.4 g |
| 9 | 9 | 23.4 g | 2.7 g |
| 10 | 10 | 23.1 g | 3.0 g |

"Empty" reverse micelles were prepared by increasing quantity of water from 1% to 10% with increment of 1% (the percentage of water is expressed by weight of water/total volume of the composition, density of 0.94). The percentage of absolute ethanol (5%) and phytosterol (2.5%) (weight/total weight of the composition) were unchanged for all these products.

The formation of thermodynamically stable microemulsions was evaluated by the visual determination of their limpidity.

Lattice parameters are obtained by X-ray diffraction and they are assumed to correspond to the size of reverse micelles of the invention. Samples were introduced in 1.5 mm diameter glass capillaries and a transmission configuration was used. A cupper rotating anode X-Ray source (functioning at 4 kW) with a multilayer focusing "Osmic" monochromator giving high flux ($10^8$ photons/sec) and punctual collimation were employed. An "Image plate" 2D detector was used. Diffraction curves were obtained giving diffracted intensity as a function of the wave vector q. Diffracted intensity was corrected by exposition time, transmission and intensity background coming from diffusion by an empty capillary. Reverse micelle sizes were calculated with the formula: $d=2\pi/q_{max}$ (q max is the wave vector corresponding to the maximal diffracted intensity).

Diffraction curves of 10 samples prepared according to above procedure are shown in FIG. 1a, which clearly demonstrates that between 1% and 6% of incorporated water, the $q_{max}$ value decreases when the percentage of water increases. FIG. 1b shows that between 1% and 6% of incorporated water, the size of reverse micelles increases from 3.1 to 3.7 nm when the percentage of water increases. In contrast, from 7% of incorporated water, the size of reverse micelles stops increasing.

Furthermore, the visual analysis shows that from 1 to 5% of incorporated water, the products are limpid. From 6% of water, the products become more and more turbid.

These results clearly show that formulations formed in absence of lecithin are unstable over a certain amount of water (6%). They additionally show that the micelles formulated without lecithin cannot exceed a given size even when increasing the amount of water in the formulation.

Example 2

Evaluation of Water Incorporation Impact on Formation and Size of Reverse Micelles in Presence of Lecithin The aim of this study was to evaluate by X ray diffraction method and visual determination the impact of water content on the formation of thermodynamically stable microemulsion and the size of reverse micelles dispersed therein in presence of increasing rate of lecithin.

3 formulations of reverse micelles with different percentages of water and lecithin were prepared according to the procedure below.

Commercially available lecithin was dissolved in 8.5 g absolute ethanol by magnetic stirring at 300 r/min for 10 minutes at room temperature. 2.3 g of phytosterol were added to the mixture and stirred in the same conditions. Glycerol monooleate was added thereto and magnetic stirring was carried out at 500 r/min for 45 minutes at 37° C. to form an oil mixture. Purified water was added to the oil mixture and stirred at room temperature by magnetic stirring between 300 and 500 r/min for 30 minutes to form "empty" reverse micelles.

The different formulations are summarized in the table below

| Sample | Lecithin | Glycerol monooleate | Water | Oil mixture |
|---|---|---|---|---|
| 11 | 0 g (0%) | 79.3 g | 20.4 mg (4%) | 453.9 mg |
| 12 | 9.4 g (10%) | 64.8 g | 45.0 mg (9%) | 433.8 mg |
| 13 | 14.1 g (15%) | 57.0 g | 60.0 mg (12%) | 423.3 mg |

"Empty" reverse micelles were prepared by varying amount of water from 4% (sample 11) to 12% (sample 13) and lecithin from 0% (sample 11) to 15% (sample 13). Lecithin content is calculated from weight of lecithin/total weight of the composition and water content from weight of water/total volume of the composition (density of 0.94). The percentage of phytosterol was 2.5% (weight of phytosterol/total weight of the composition) and that of absolute ethanol was 9% (weight of absolute ethanol/total weight of the composition) for all these samples.

The formation of thermodynamically stable microemulsions was evaluated by the visual determination of their limpidity.

The size of reverse micelles of these formulations was evaluated by X-ray diffraction experiments as described in example 1.

Diffraction curves of samples 11, 12, and 13 are shown in FIG. 2a which clearly demonstrates that the diffracted intensity increases and the $q_{max}$ value decreases when the percentage of lecithin increases from 0 to 15%. FIG. 2b demonstrates that the size of reverse micelles increases from 3.1 to 4.5 nm when the percentage of lecithin increases from 0 to 15%. The visual analysis shows that these formulations are limpid.

Consequently, these experiments show that the addition of 15% of lecithin allows the formation of thermodynamically stable microemulsions with reverse micelle size of 4.5 nm and high percentages of water (12%). Addition of lecithin thus solves the drawbacks of reverse micelles formulated in absence of lecithin described in example 1.

Example 3

Evaluation of GAPDH siRNA Incorporation Impact on Formation and Size of Reverse Micelles The aim of this study was to evaluate by X ray diffraction method and visual determination the impact of GAPDH siRNA content on the formation of thermodynamically stable microemulsions and the size of reverse micelles dispersed therein in presence of lecithin.

GAPDH siRNA is a double stranded siRNA comprising 21 nucleotides and designed to allow gene silencing of GAPDH gene.

4 formulations of reverse micelles with different concentrations of GAPDH siRNA were prepared according to the procedure below.

A siRNA solution containing GAPDH siRNA was added to the oil mixture prepared according to sample 13 and stirred at room temperature by magnetic stirring between 300 and 500 r/min for 30 minutes to form reverse micelles containing GAPDH siRNA.

The different formulations are summarized in the table below:

| Sample | siRNA solution or water | GAPDH siRNA | Oil mixture | GADPH concentration |
|---|---|---|---|---|
| A | 59.6 mg | 150 µg | 411.3 mg | 300 µg/ml |
| B | 60.9 mg | 228 µg | 414.8 mg | 450 µg/ml |
| C | 61.1 mg | 303 µg | 414.5 mg | 600 µg/ml |
| D | 59.9 mg | 479 µg | 413.2 mg | 950 µg/ml |
| 13 | 60.0 mg | 0 µg | 423.3 mg | 0 µg/ml |

Reverse micelles were prepared by increasing concentrations of GAPDH siRNA from 0 (sample 13) to 950 µg/ml (sample D). The percentage of phytosterol was 2.5% (weight of phytosterol/total weight of the composition), that of absolute ethanol was 9% (weight of absolute ethanol/total weight of the composition), that of water was 12% (weight of water/total volume of the composition, density of 0.94) and that of lecithin was 15% (weight of lecithin/total weight of the composition) for all these samples.

The formation of thermodynamically stable microemulsions was evaluated by the visual determination of their limpidity.

The size of reverse micelles of these formulations was evaluated by X-ray diffraction experiments as described in example 1.

FIG. 3 shows diffraction curves of samples 13, A, B, C and D. The $q_{max}$ value is the same for all the samples in spite of an increase of GAPDH siRNA concentration. The reverse micelle size is calculated at 4.5 nm for all these samples. The visual analysis shows that these formulations are limpid.

These experiments show that the addition of GAPDH siRNA does not disturb the formation of thermodynamically stable microemulsions and does not change the size of reverse micelles dispersed therein.

Example 4

Evaluation of In Vivo Biodistribution of Fluorescent Alexa 700-Cyclin B1 (ClB1) siRNA Formulated in Reverse Micelles The aim of this study was to evaluate by animal imaging technique the biodistribution of Alexa 700-ClB1 siRNA formulated in reverse micelles according to the procedure below (sample E) when delivered by rectal route compared to same dosage of unformulated said siRNA in solution delivered by intravenous route.

Alexa 700-ClB1 siRNA is a double stranded siRNA comprising 21 nucleotides and designed to be fluorescent.

Sample E: 14.1 g of lecithin were dissolved in 8.5 g absolute ethanol by magnetic stirring at 300 r/min for 10 minutes at room temperature. 2.3 g of phytosterol were added to the mixture and stirred in the same conditions. 57.0 g of glycerol monooleate were added thereto and magnetic stirring was carried out at 500 r/min for 45 minutes at 37° C. 48 mg of a siRNA solution containing 100 µg of Alexa 700-ClB1 siRNA were added to 328.7 mg of the oil mixture and stirred at room temperature by magnetic stirring at 700 r/min for 45 minutes to form reverse micelles containing 250 µg Alexa 700-ClB1 siRNA/ml (density of 0.94).

Administered Products:

Sample E: reverse micelles prepared according to above procedure at 250 µg Alexa 700-ClB1 siRNA/ml, delivered at 2 ml/kg by rectal route Unformulated Alexa 700-ClB1 siRNA: naked siRNA in solution at 50 µg Alexa 700-ClB1 siRNA/ml, delivered at 10 ml/kg by intravenous route Unformulated naked Alexa 700-ClB1 siRNA or reverse micelles formulated with said siRNA were administered once at 500 µg/kg (10 µg) in anesthetised nude mice. Naked Alexa 700-ClB1 siRNA solution was administrated intravenously in the tail vein and reverse micelles formulated siRNA were administrated slowly with a pipette into the lower rectum, immediately after the anal sphincter.

Mice were placed under camera at 660 nm and side and ventral pictures were taken at 0, 15 min, 1 h, 2 h, 4 h, 5 h and 24 h to visualize fluorescence intensity biodistribution.

Results are shown in FIGS. 4a and 4b. FIG. 4a demonstrates a rapid absorption of naked siRNA after iv injection. The maximal fluorescence intensity is observed 15 minutes post-administration and decreased rapidly.

In contrast, the FIG. 4b shows that siRNA formulated in reverse micelles and administered by rectal route, is widely distributed in the entire body of the animal with a fluorescence peak at around 4 hours and a very slow elimination.

The above experiment demonstrates that siRNA formulated in reverse micelles can be delivered in vivo and that the reverse micelles formulation highly increases siRNA protection and life span.

Example 5

Evaluation of In Vivo Efficacy of GAPDH siRNA Formulated in Reverse Micelles Formulations to Inhibit GAPDH Gene Expression The aim of this study was to evaluate liver GAPDH gene silencing efficacy of GAPDH siRNA formulated in reverse micelles prepared according to the procedures below (samples F and G) when delivered by rectal route in C57Bl/6J mice.

GAPDH siRNA is a double stranded siRNA comprising 21 nucleotides and designed to allow gene silencing of GAPDH gene.

Sample F: 2.3 g of cholesterol were dissolved in 8.5 g of absolute ethanol by magnetic stirring at 300 r/min for 15 minutes at room temperature. 79.2 g of glycerol monooleate were added thereto and magnetic stirring was carried out at 500 r/min for 45 minutes at 37° C. to form oil mixture. 40.0 mg of a siRNA solution containing 301 µg of GAPDH siRNA were added to 904.0 mg of the oil mixture and stirred at room temperature by magnetic stirring between 300 and 500 r/min for 30 minutes to form reverse micelles containing 300 µg GAPDH siRNA/ml (density of 0.94).

Sample G: 6.6 g of lecithin were dissolved in 8.5 g of absolute ethanol by magnetic stirring at 300 r/min for 10 minutes at room temperature. 2.3 g of cholesterol were added to the mixture and stirred in the same conditions. 67.7 g of glycerol monooleate were added thereto and magnetic stirring was carried out at 500 r/min for 45 minutes at 37° C. 45.2 mg of a siRNA solution containing 286 µg of GAPDH siRNA were added to 852.7 mg of the oil mixture and stirred at room temperature by magnetic stirring between 300 and 500 r/min for 30 minutes to form reverse micelles containing 300 µg GAPDH siRNA/ml (density of 0.94).

Sample 14: 40.5 mg of purified water was added to 900.6 mg of the oil mixture prepared according to sample F and stirred at room temperature by magnetic stirring between 300 and 500 r/min for 30 minutes to form "empty" reverse micelles.

Administered Products:

Sample F: reverse micelles prepared according to above procedure at 300 µg GAPDH siRNA/ml, delivered at 1 ml/kg by rectal route for 3 days Sample G: reverse micelles prepared according to above procedure at 300 µg GAPDH siRNA/ml, delivered at 1 ml/kg by rectal route for 3 days Sample 14: "empty" reverse micelles prepared according to above procedure, delivered at 1 ml/kg by rectal route for 3 days As described in table below, both formulations of reverse micelles containing GAPDH siRNA were delivered at 600 µg/kg (300 µg/kg twice a day) for 3 days in C57Bl/6J mice (groups 2 and 3, 3 mice per group). These products were delivered slowly with a pipette into the lower rectum, immediately after the anal sphincter. Mice untreated or treated with "empty" reverse micelles were used as controls (groups 1 and 4) (sample 14).

Mice were sacrificed 24 hours after the last administration. Livers were then harvested and frozen. Total RNA was extracted by TRIzol®/chloroform method and GAPDH mRNA expression was evaluated by quantitative RT-PCR, relative to a normalizer gene (ubiquitin).

Figure 5:
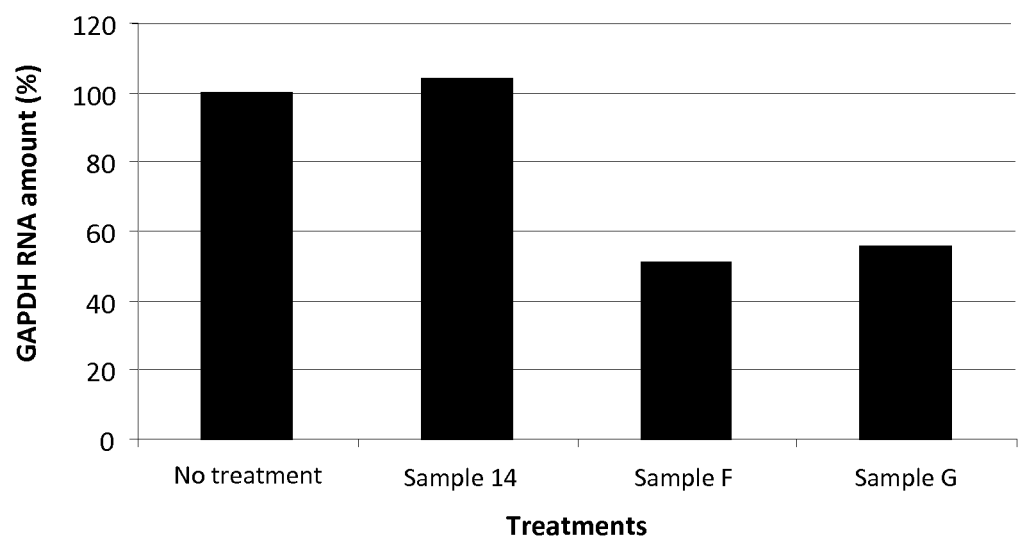
FIG. 5: In vivo evaluation of liver GAPDH gene inhibition.

Results are shown in FIG. 5 which demonstrates the in vivo efficacy of GAPDH siRNA formulated in reverse micelles containing cholesterol (sample F) to reduce liver GAPDH gene expression. The addition of lecithin in sample G shows similar efficacy to reduce GAPDH gene expression. In contrast, the "empty" reverse micelles (sample 14) are ineffective at decreasing GAPDH gene expression. Reverse micelles according to the invention are thus as efficient as those not containing lecithin for delivery of such quantities of nucleic acids. They additionally allow delivery of greater amounts of nucleic acids than reverse micelles without lecithin.

| Groups | Animal Number | Treatment | Delivered dose (μg/kg/d) | Delivered volume (ml/kg/d) |
|---|---|---|---|---|
| 1 | 3 | No treatment | 0 | — |
| 2 | 3 | Sample F | 600 | 2 × 1 |
| 3 | 3 | Sample G | 600 | 2 × 1 |
| 4 | 3 | Sample 14 | 0 | 2 × 1 |

Example 6

Evaluation of In Vivo Efficacy of Ubiquitin Ligase Atrogin 1/Muscle Atrophy F-Box Sequence (MAFbx) siRNA Formulated in Reverse Micelles to Inhibit MAFbx Gene Expression The aim of this study was to evaluate MAFbx gene silencing efficacy of MAFbx si1 or si2 siRNA formulated in reverse micelles according to the procedures below (samples H and I) when delivered by rectal route compared to same dosage of unformulated MAFbx si1 siRNA delivered intravenously, in an induced mice model of MAFbx over expression.

MAFbx si1 and si2 siRNA are double stranded siRNAs respectively comprising 19 and 21 nucleotides and designed to allow gene silencing of MAFbx gene.

Sample H, 14.1 g of lecithin were dissolved in 8.5 g absolute ethanol by magnetic stirring at 300 r/min for 10 minutes at room temperature. 2.3 g of phytosterol were added to the mixture and stirred in the same conditions. 57.0 g of glycerol monooleate were added thereto and magnetic stirring was carried out at 500 r/min for 45 minutes at 37° C. 117.3 mg of a siRNA solution containing 303 μg of MAFbx s1 siRNA were added to 833.8 mg of the oil mixture and stirred at room temperature by magnetic stirring between 300 and 500 r/min for 30 minutes to form reverse micelles containing 300 μg MAFbx si1 siRNA/ml (density of 0.94).

Sample I: 2.3 g of phytosterol were dissolved in 8.5 g of absolute ethanol by magnetic stirring at 300 r/min for 15 minutes at room temperature. 79.2 g of glycerol monooleate were added thereto and magnetic stirring was carried out at 500 r/m for 45 minutes at 37° C. to form oil mixture. 39.5 mg of a siRNA solution containing 302 μg of MAFbx si2 siRNA were added to 905.4 mg of the oil mixture and stirred at room temperature by magnetic stirring between 300 and 500 r/min for 30 minutes to form reverse micelles containing 300 μg MAFbx si2 siRNA/ml (density of 0.94).

Administered Products:

Sample H: reverse micelles prepared according to the above procedure at 300 μg MAFbx si1 siRNA/ml, delivered at 1 ml/kg by rectal route on days 1 and 2

Sample I: reverse micelles prepared according to the above procedure at 300 μg MAFbx si2 siRNA/ml, delivered at 1 ml/kg by rectal route on days 1 and 2

Unformulated MAFbx si1 siRNA: naked siRNA in solution at 300 μg/ml, delivered at 1 ml/kg by intravenous route on day 1 and at 150 μg/ml delivered at 1 ml/kg the second day.

B6CBA F1 mice were treated as described in table below. Reverse micelles formulated with MAFbx si1 or 2 siRNA (samples H and I) were delivered at 300 μg/kg by rectal route once a day for 2 days. These products were delivered slowly with a pipette into the lower rectum, immediately after the anal sphincter. Following this treatment, a 2 days starvation for food was applied to induce skeletal muscular atrophy and overexpression of MAFbx (groups 5 and 7, 8 mice per group). Mice administered with the same treatment (samples H and I) but not starved were used as controls (groups 4 and 6, 4 mice per group). Another group of 8 mice (group 3) was treated with unformulated naked MAFbx si1 siRNA by intravenous route in the tail vein at 300 μg/kg the first day and 150 μg/kg the second day followed by a 2 days food starvation. Untreated mice starved or not for food, were used as controls (groups 1 and 2, 8 mice per group).

All mice were sacrificed on day 5, and Tibialis Anterior (TA) muscles were harvested and frozen. Total RNA was extracted by TRIzol®/chloroform method and MAFbx mRNA expression was evaluated relative to normalizer ribosomal gene (RPS9) by quantitative RT-PCR using mini Opticon Real Time PCR system (Biorad).

Figure 6:
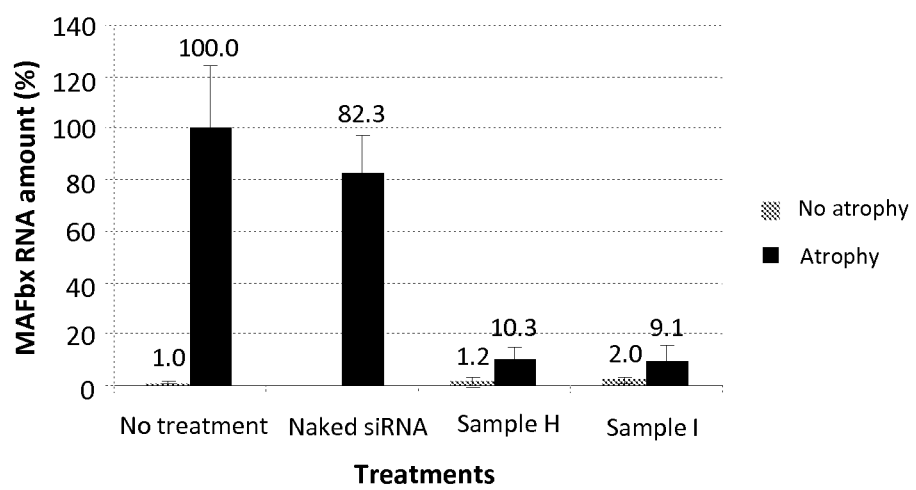
FIG. 6: In vivo evaluation of muscle MAFBx gene inhibition.

Results of quantitative PCR are shown in FIG. 6, which clearly demonstrates the efficacy of reverse micelles formulated with MAFbx siRNA to reduce the MAFbx gene overexpression. Around 90% reduction in MAFbx mRNA levels is observed in animal treated with samples H and I compared to untreated animal. Reverse micelles according to the invention are thus as efficient as those not containing lecithin for delivery of such quantities of nucleic acids. They additionally allow delivery of greater amounts of nucleic acids than reverse micelles without lecithin.

| Groups | Animal Number | Animal type | Treatment | Active compounds | Delivered dose (μg/kg/d) | Delivered volume (ml/kg/d) |
|---|---|---|---|---|---|---|
| 1 | 8 | No food deprivation | No treatment | — | 0 | — |
| 2 | 8 | Food deprivation | No treatment | — | 0 | — |
| 3 | 8 | Food deprivation | Naked siRNA | MAFbx si1 siRNA | 300 and 150 | 1 |
| 4 | 4 | No food deprivation | Sample H | MAFbx si1 siRNA | 300 | 1 |
| 5 | 8 | Food deprivation | Sample H | MAFbx si1 siRNA | 300 | 1 |
| 6 | 4 | No food deprivation | Sample I | MAFbx si2 siRNA | 300 | 1 |
| 7 | 8 | Food deprivation | Sample I | MAFbx si2 siRNA | 300 | 1 |

Example 7

Evaluation of In Vivo Efficacy of siRNA Targeting Proprotein Convertase Subtilisin/Kexin Type 9 (PCSK9) siRNA Formulated in Reverse Micelles to Inhibit PCSK9 Protein Expression The aim of this study was to evaluate the efficacy of PCSK9 siRNA formulated in reverse micelles according to the procedure below (sample J) to decrease PCSK9 protein expression when delivered by rectal route compared to same dosage of unformulated PCSK9 siRNA delivered intravenously in C57Bl/6J mice.

PCSK-9 siRNA is a double stranded siRNA comprising 21 nucleotides and designed to allow inhibition of PCSK9 protein expression.

Sample J: 14.3 g of lecithin were dissolved in 8.6 g absolute ethanol by magnetic stirring at 300 r/min for 10 minutes at room temperature. 2.4 g of phytosterol were added to the mixture and stirred in the same conditions. 57.8 g of glycerol monooleate were added thereto and magnetic stirring was carried out at 500 r/min for 60 minutes at 37° C. 694.8 mg of a siRNA solution containing 5797 µg of PCSK9 siRNA were added to 4819.4 mg of the oil mixture and stirred at room temperature by magnetic stirring between 300 and 500 r/min for 30 minutes to form reverse micelles containing 1000 µg PCSK9 siRNA/ml (density of 0.95).

Sample 15: 2.4 g of purified water was added to 16.6 g of the oil mixture prepared according to sample J and stirred at room temperature by magnetic stirring between 300 and 500 r/min for 30 minutes to form "empty" reverse micelles.

Administered Products:

Sample J: reverse micelles prepared according to above procedure at 1000 µg PCSK9 siRNA/ml, delivered at 1 ml/kg by rectal route for 10 days Sample 15: "empty" reverse micelles, delivered at 1 ml/kg by rectal route for 10 days Unformulated PCSK9 siRNA: naked siRNA in solution at 1000 µg PCSK9 siRNA/ml, delivered at 1 ml/kg by intravenous route for 10 days Saline buffer delivered at 1 ml/kg by intravenous route for 10 days C57Bl/6J mice (7 or 8 mice per group) were treated as described in table below. PCSK9 siRNA formulated in sample J delivered at 1000 µg/kg (group 1) and "empty" reverse micelle (sample 15), used as control (group 2), were administered by rectal route once a day for 10 days. These products were delivered slowly with a pipette into the lower rectum, immediately after the anal sphincter. Animals treated intravenously for 10 days with unformulated naked PCSK9 siRNA (group 3) or saline buffer (group 4) were also used as controls.

All mice were sacrificed on day 11. Livers were harvested and frozen. PCSK9 protein expression was determined by an ELISA method (R&D Systems) in accordance with the manufacturer instructions.

Figure 7:
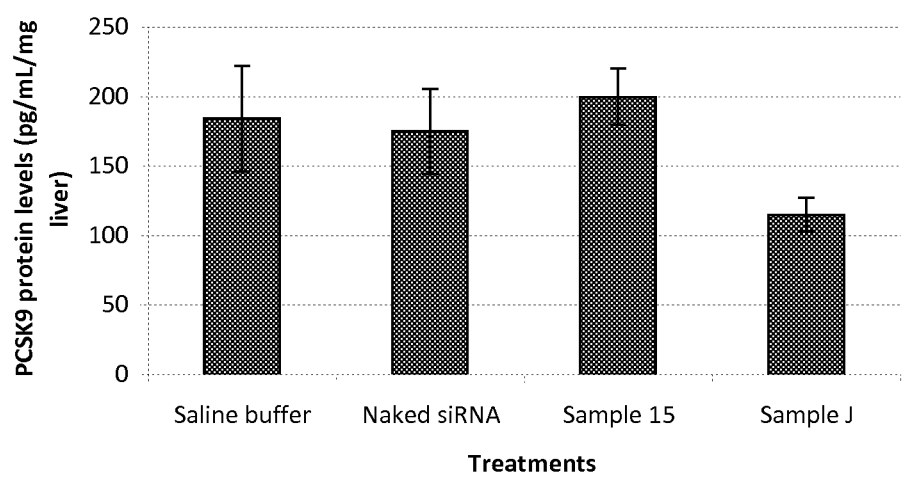
FIG. 7: In vivo evaluation of liver PCSK9 protein inhibition.
Figure 8:
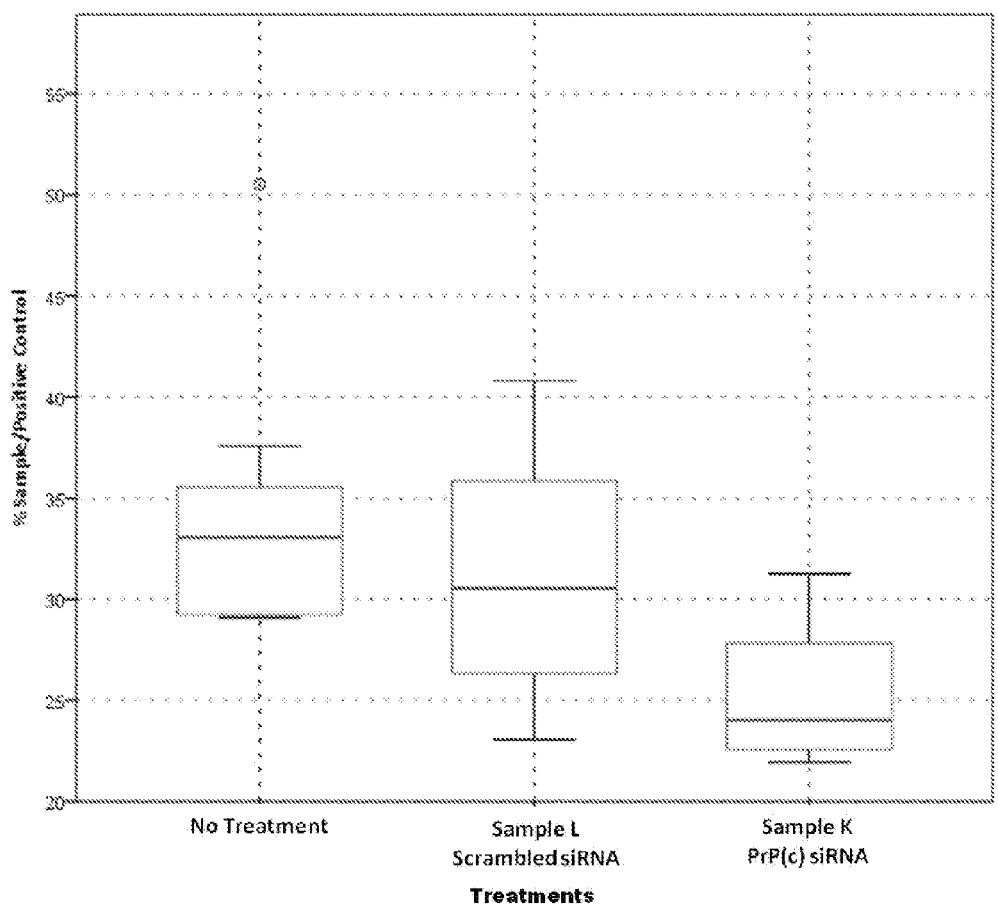
FIG. 8: In vivo evaluation of brain PrP(C) protein inhibition.

Results are shown in FIG. 7 wish which clearly demonstrate the efficacy of treatment with reverse micelles formulated with PCSK9 siRNA (sample J) to reduce PCSK9 protein expression in the liver compared to empty reverse micelles (sample 15). Furthermore, the formulation of PCSK9 siRNA in reverse micelles according to the invention affords a better efficacy of said siRNA to reduce PCSK9 protein expression in the liver compared to naked PCSK9 siRNA.

| Groups | Animal Number | Treatment | Delivered dose (µg/kg/d) | Delivered volume (ml/kg/d) |
|---|---|---|---|---|
| 1 | 8 | Sample J | 1000 | 1 |
| 2 | 8 | Sample 15 | 0 | 1 |
| 3 | 7 | Naked siRNA | 1000 | 1 |
| 4 | 7 | Saline buffer | 0 | 1 |

Example 8

Evaluation of In Vivo Efficacy of PrP(C) siRNA Formulated in Reverse Micelles to Inhibit PrP(C) Protein Expression The aim of this study was to evaluate the efficacy of normal prion protein PrP(C) siRNA formulated in reverse micelles according to the procedure below (sample K) when delivered by rectal route to inhibit PrP(C) protein expression in brain of C57Bl/6J mice.

PrP(C) siRNA is a double stranded siRNA comprising 21 nucleotides and designed to allow inhibition of PrP(C) protein expression.

Sample K: 14.1 g of lecithin were dissolved in 8.5 g absolute ethanol by magnetic stirring at 300 r/min for 15 minutes at room temperature. 2.3 g of phytosterol were added to the mixture and stirred in the same conditions 57.1 g of glycerol monooleate were added thereto and magnetic stirring was carried out at 500 r/min for 45 minutes at 37° C. 184.0 mg of a siRNA solution containing 932 μg of PrP(C) siRNA were added to 1233.6 mg of the oil mixture and stirred at room temperature by magnetic stirring between 300 and 500 r/min for 60 minutes to form reverse micelles containing 618 μg PrP(C) siRNA/ml (density of 0.94).

Scrambled (SC) siRNA is a double stranded siRNA comprising 21 nucleotides and designed not to allow any modulation of PrP(C) protein expression.

Sample L: 184.2 mg of a siRNA solution containing 933 μg of SC siRNA were added to 1233.8 mg of the oil mixture prepared according to sample K and stirred at room temperature by magnetic stirring between 300 and 500 r/min for 60 minutes to form reverse micelles containing 618 μg SC siRNA/ml (density of 0.94).

Administered Products:

Sample K: reverse micelles prepared according to above procedure at 618 μg PrP(C) siRNA/ml, delivered at 1 ml/kg by rectal route for 12 days Sample L: reverse micelles prepared according to above procedure at 618 μg SC siRNA/ml, delivered at 1 ml/kg by rectal route for 12 days C57Bl/6J mice were treated as described in table below. PrP(C) and SC siRNA formulated in reverse micelle (samples K and L) were delivered at 618 μg/kg (groups 2 and 3, 10 mice per group). Both products were delivered slowly with a pipette into the lower rectum, immediately after the anal sphincter once a day for 12 days (weekends excluded). Untreated animals were also used as controls (group 1, 10 mice per group).

All mice were sacrificed on day 13. Brains were harvested and frozen. PrP(C) protein levels were determined by an ELISA method (SPI BIO) in accordance with the manufacturer instructions.

Results are shown in FIG. 8 which clearly demonstrates the efficacy of PrP(C) siRNA formulated in reverse micelles (sample K) to cross the blood brain barrier and reduce brain protein expression of PrP(C). In contrast, reverse micelles formulated with a non specific scrambled siRNA (sample L) have no effect on brain expression of PrP(C).

| Groups | Animal Number | Treatment | Active compounds | Delivered dose (µg/kg/d) | Delivered volume (ml/kg/d) |
|---|---|---|---|---|---|
| 1 | 10 | No treatment | — | 0 | — |
| 2 | 10 | Sample L | Scrambled siRNA | 618 | 1 |
| 3 | 10 | Sample K | PrP(C) siRNA | 618 | 1 |

Example 9

Formulation of Reverse Micelles According to the Invention with Antisens Oligonucleotides The aim of this study was to formulate chemically modified antisens oligonucleotides (ASON) in reverse micelles according to the invention.

DMPK2467U is a gapmer ASON comprising 20 nucleotides.

Sample M: 14.3 g of lecithin were dissolved in 8.6 g absolute ethanol by magnetic stirring at 300 r/min for 15 minutes at room temperature. 2.4 g of phytosterol were added to the mixture and stirred in the same conditions 57.8 g of glycerol monooleate were added thereto and magnetic stirring was carried out at 500 r/min for 60 minutes at 37° C. 724.6 mg of a ASON solution containing 5973 µg of DMPK2467U ASON were added to 4984.0 mg of the oil mixture and stirred at room temperature by magnetic stirring between 300 and 500 r/min for 30 minutes to form reverse micelles containing 994 µg DMPK2467U ASON/ml (density of 0.95).

DMPKGD65 is a gapmer ASON comprising 20 nucleotides.

Sample N: 715.6 mg of a ASON solution containing 5933 µg of DMPKGD65 ASON were added to 4986.2 mg of the oil mixture prepared according to sample M and stirred at room temperature by magnetic stirring between 300 and 500 r/min for 30 minutes to form reverse micelles containing 988 µg DMPKGD65 ASON/ml (density of 0.95).

REFERENCES

Altmann K. H., Fabbro D., Dean N. M., Geiger T., Monia B. P., Muller M. and Nicklin P. Second-generation antisense oligonucleotides: structure-activity relationships and the design of improved signal-transduction inhibitors. *Biochem Soc Trans,* 1996, 24 (3):630-7.

Brinkman B. M. Splice variants as cancer biomarkers. *Clin Biochem,* 2004, 37(7):584-94.

Brummelkamp, T. R., Bernards, R., and Agami, R. (2002); a system for stable expression of short interfering RNAs in mammalian cells. Science 296, 550-553

Chan J. H., Lim S, and Wong W. S. Antisense oligonucleotides: from design to therapeutic application. *Clin Exp Pharmacol Physiol,* 2006, 33(5-6): 533-40.

Chauveau F., Pestourie C. and Tavitian B. [Aptamers: selection and scope of applications]. *Pathol Biol* (Paris), 2006, 54(4):251-8.

Drolet D. W., Nelson J., Tucker C. E., Zack P. M., Nixon K., Bolin R., Judkins M. B., Dykxhoorn D. M., Novina C. D., Sharp Philip A. (2003) Killing the messenger: short RNAs that silence gene expression. Nat Rev Mol Cell Biol. 4, 457-467

Egholm M., Buchardt O., Christensen L., Behrens C., Freier S. M., Driver D. A., Berg R. H., Kim S. K., Norden B. and Nielsen P. E. PNA hybridizes to complementary oligonucleotides obeying the Watson-Crick hydrogen-bonding rules. *Nature,* 1993, 365(6446):566-8.

Gallo M., Montserrat J. M. and Iribarren A. M. Design and applications of modified oligonucleotides. *Braz J Med Biol Res,* 2003, 36(2):143-51.

Kang S. H., Cho M. J. and Kole R. Up-regulation of luciferase gene expression with antisense oligonucleotides: implications and applications in functional assay development. *Biochemistry,* 1998, 37(18):6235-9.

Kim Y. M., Choi K. H., Jong Y. J., Yu J. and Jeong S. Specific modulation of the anti-DNA autoantibody-nucleic acids interaction by the high affinity RNA aptamer. *Biochem Biophys Res Commun,* 2003, 300(2):516-23.

Kurreck J. Antisense technologies. Improvement through novel chemicalmodifications. *Eur J Biochem,* 2003, 270 (8):1628-44.

McCaffrey A. P., Meuse L., Pham T. T., Conklin D. S., Hannon G. J. and Kay M. A. RNA interference in adult mice. *Nature,* 2002, 418(6893):38-9.

Mercatante D. R., Bortner C. D., Cidlowski J. A. and Kole R. Modification of alternative splicing of Bcl-x pre-mRNA in prostate and breast cancer cells. analysis of apoptosis and cell death. *J Biol Chem,* 2001, 276(19):16411-7.

Pendergrast P. S., Marsh H. N., Grate D., Healy J. M. and Stanton M. Nucleic acid aptamers for target validation and therapeutic applications. *J Biomol Tech,* 2005, 16(3):224-34.

Rhodes A., Deakin A., Spaull J., Coomber B., Aitken A., Life P. and Rees S. The generation and characterization of antagonist RNA aptamers to human oncostatin M. *J Biol Chem,* 2000, 275(37):28555-61.

Rimmele M. Nucleic acid aptamers as tools and drugs: recent developments. *Chembiochem,* 2003, 4(10):963-71.

Sazani P. and Kole R. Modulation of alternative splicing by antisense oligonucleotides. *Prog Mol Subcell Biol,* 2003, 31(217-39.

Singh S. K., Kumar R. and Wengel J. Synthesis of Novel Bicyclo[2.2.1] Ribonucleosides: 2'-Amino- and 2'-Thio-LNA Monomeric Nucleosides. *J Org Chem,* 1998, 63(18): 6078-6079.

Srebrow A. and Kornblihtt A. R. The connection between splicing and cancer. *J Cell Sci,* 2006, 119(Pt 13):2635-41.

Summerton J. and Weller D. Morpholino antisense oligomers: design, preparation, and properties. *Antisense Nucleic Acid Drug Dev,* 1997, 7(3):187-95.

Venables J. P. Unbalanced alternative splicing and its significance in cancer. *Bioessays,* 2006, 28(4):378-86.

Wacheck V. and Zangemeister-Wittke U. Antisense molecules for targeted cancer therapy. *Crit. Rev Oncol Hematol,* 2006, 59(1):65-73.

White R. R., Sullenger B. A. and Rusconi C. P. Developing aptamers into therapeutics. *J Clin Invest,* 2000, 106(8): 929-34.

The invention claimed is:

1. A reverse micelle system comprising at least one nucleic acid, a sterol, an acylglycerol, a phospholipid or a sphingolipid, an alcohol and water, wherein the weight ratio of phospholipid or sphingolipid/acylglycerol is from 0.05 to 0.40 and said reverse micelle system comprises lecithin as the phospholipid and has an aqueous core of between 3.7 and 4.5 nm.

2. The reverse micelle system according to claim 1, wherein said reverse micelle system has an aqueous core of 4 5 nm.

3. A reverse micelle system comprising at least one nucleic acid, a sterol, an acylglycerol, a phospholipid or a sphingolipid, an alcohol and water, wherein the weight ratio of phospholipid or sphingolipid/acylglycerol is from 0.05 to 0.40, said reverse micelle system comprises lecithin as the phospholipid and said reverse micelle system has an aqueous core of between 3 and 5 nm.

4. A reverse micelle system comprising at least one nucleic acid, a sterol, an acylglycerol, a phospholipid or a sphingolipid, an alcohol and water, wherein the weight ratio of phospholipid or sphingolipid/acylglycerol is from 0.05 to 0.40, said reverse micelle system comprises lecithin as the phospholipid and said reverse micelle system has an aqueous core of between 3.5 and 5 nm.

* * * * *

UNITED STATES PATENT AND TRADEMARK OFFICE
CERTIFICATE OF CORRECTION

| | | |
|---|---|---|
| PATENT NO. | : 8,877,237 B2 | Page 1 of 1 |
| APPLICATION NO. | : 13/636452 | |
| DATED | : November 4, 2014 | |
| INVENTOR(S) | : Jean-Claude Maurel | |

It is certified that error appears in the above-identified patent and that said Letters Patent is hereby corrected as shown below:

In the Specification

Column 6,
Lines 36-37, "Gattefosse" should read --Gattefossé--.

Column 11,
Line 9, "strech" should read --stretch--.

Column 13,
Line 61, "MAFBx" should read --MAFbx--.

Column 14,
Line 53, "cupper" should read --copper--.

Column 16,
Line 40, "GADPH concentration" should read --GAPDH concentration--.

Column 19,
Line 32, "MAFBx" should read --MAFbx--.

Column 23,
Line 15, "Antisens" should read --Antisense--.
Line 18, "antisens" should read --antisense--.

Column 24,
Line 19, "Jong" should read --Jang--.
Line 24, "chemicalmodifications." should read --chemical modifications.--.

Signed and Sealed this
Fourth Day of August, 2015

Michelle K. Lee
*Director of the United States Patent and Trademark Office*